US012520411B2

(12) United States Patent
Koppisetty et al.

(10) Patent No.: US 12,520,411 B2
(45) Date of Patent: Jan. 6, 2026

(54) SYSTEMS AND METHODS FOR A HIGH VOLTAGE CONNECTOR ASSEMBLY FOR A MEDICAL IMAGING DEVICE

(71) Applicant: GE Precision Healthcare LLC, Waukesha, WI (US)

(72) Inventors: Kalyan Koppisetty, Waukesha, WI (US); Edward Emaci, Brookfield, WI (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 182 days.

(21) Appl. No.: 18/430,520

(22) Filed: Feb. 1, 2024

(65) Prior Publication Data

US 2025/0254784 A1 Aug. 7, 2025

(51) Int. Cl.

| | |
|---|---|
| ***H05G 1/10*** | (2006.01) |
| ***A61B 6/00*** | (2006.01) |
| ***A61B 6/40*** | (2024.01) |
| ***H01R 13/73*** | (2006.01) |

(52) U.S. Cl.

CPC ................. *H05G 1/10* (2013.01); *A61B 6/40* (2013.01); *A61B 6/56* (2013.01); *H01R 13/73* (2013.01); *H01R 2201/12* (2013.01)

(58) Field of Classification Search

CPC .. A61B 6/40; A61B 6/56; H01R 13/73; H01R 2201/12; H01J 35/16; H01J 29/925; H01J 37/241; H01J 37/248; H01J 35/165; H01G 1/02; H01G 1/10

See application file for complete search history.

(56) References Cited

FOREIGN PATENT DOCUMENTS

CN 106376166 A * 2/2017 ............... H05G 1/02

OTHER PUBLICATIONS

Koppisetty, K. et al., "High Voltage Connector," U.S. Appl. No. 29/927,004, filed Feb. 1, 2024, 15 pages.

* cited by examiner

*Primary Examiner* — Don K Wong
(74) *Attorney, Agent, or Firm* — McCoy Russell LLP

(57) ABSTRACT

Systems and methods are provided for increasing installation efficiency and high voltage stability of high voltage connector of a medical imaging system. In one embodiment, a high voltage connector for a medical imaging system comprises a generator side interface configured to couple to a high voltage generator, a tube side interface configured to couple to an X-ray tube, and an insulated conductor flexibly coupling the generator side interface and the tube side interface, wherein the generator side interface is positionable in an installation position and an operational position.

20 Claims, 10 Drawing Sheets

SYSTEMS AND METHODS FOR A HIGH VOLTAGE CONNECTOR ASSEMBLY FOR A MEDICAL IMAGING DEVICE

FIELD

Embodiments of the subject matter disclosed herein relate to a high voltage connector assembly for interventional medical imaging.

BACKGROUND

In an X-ray tube, ionizing radiation is created by accelerating electrons in a vacuum from a cathode to an anode via an electric field. Typically, an emitter is heated by a current flowing through it, to create a plurality of electrons which may be formed as an electron beam that is accelerated towards the anode. To flow current to the emitter, an electrical interface of the X-ray tube is electrically coupled to a high voltage (HV) generator via an HV cable. In at least some applications, the HV generator is placed away from the imaging room, such as in an equipment room in another room or on another floor, with the HV cable routed a substantial distance from the HV generator to the X-ray tube. During installation, the electrical interface between the HV generator and the X-ray tube may be filled with dielectric oil for insulation, cooling, and high voltage stability.

BRIEF DESCRIPTION

In one embodiment, a high voltage connector for a medical imaging system comprises a generator side interface configured to couple to a high voltage generator, a tube side interface configured to couple to an X-ray tube, and an insulated conductor flexibly coupling the generator side interface to the tube side interface, wherein the generator side interface is positionable in an installation position and an operational position. In this way, installation and maintenance of the high voltage connector may be carried out more efficiently, and incidence of high voltage stress may be reduced, thereby increasing the performance and longevity of the X-ray tube.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
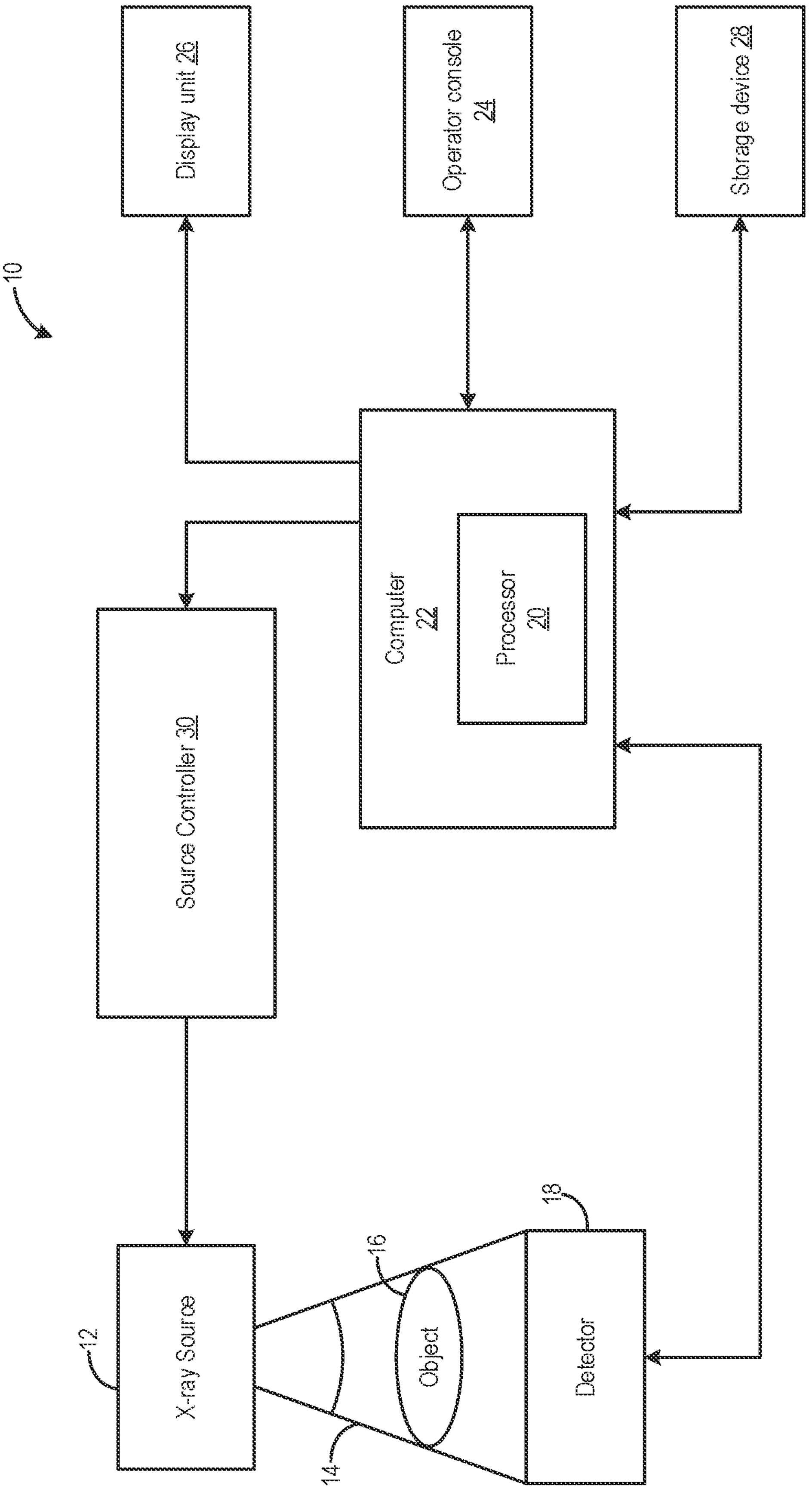
FIG. 1 shows a block diagram of an example of an imaging system.
Figure 2:
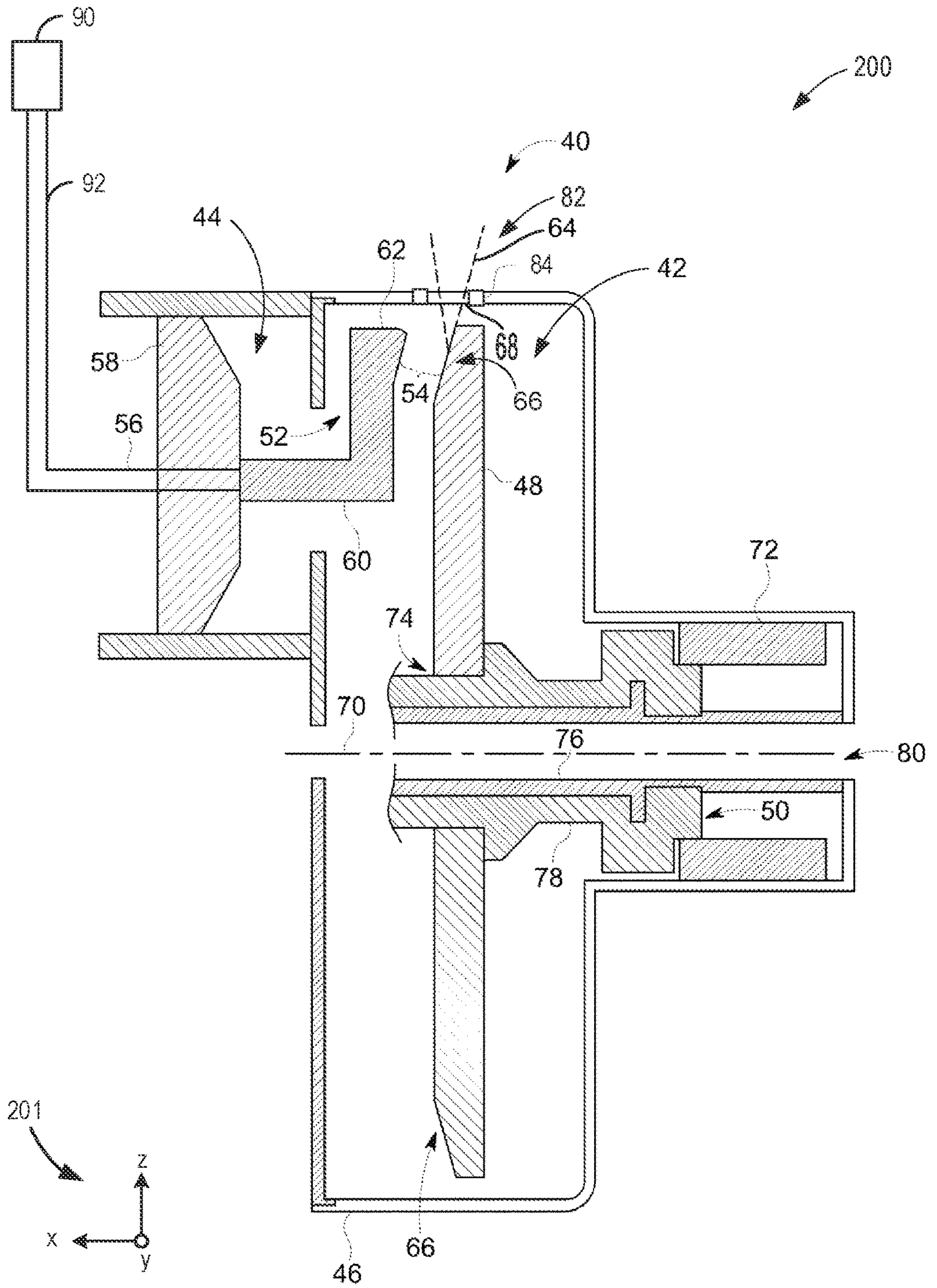
FIG. 2 shows a schematic of a cross-sectional view of an X-ray source that may be included in the imaging system of FIG. 1.
Figure 3:
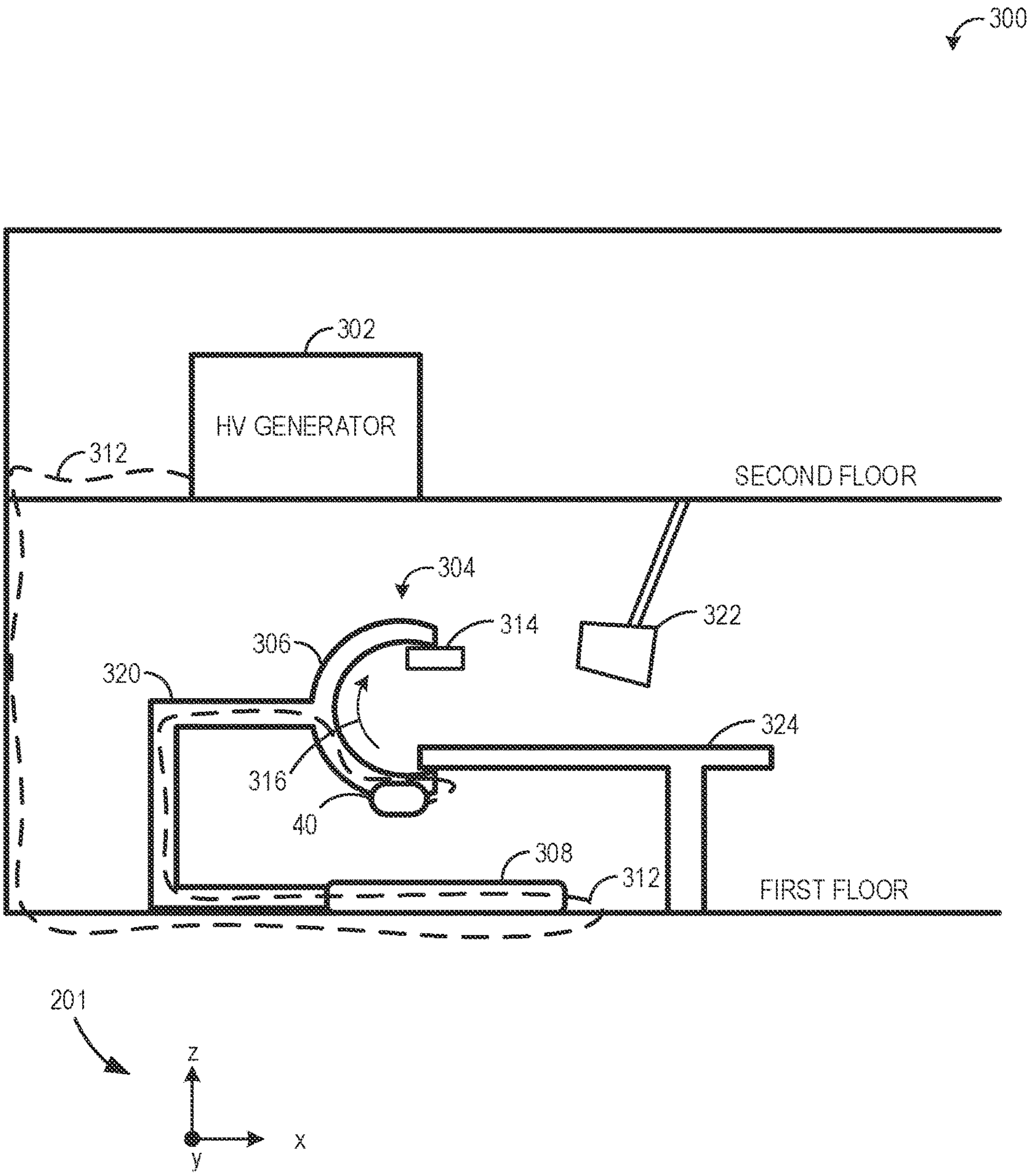
FIG. 3 shows a pictorial diagram of a high voltage (HV) generator conducting a flow of electric current to an X-ray source that may be included in the imaging system of FIG. 1.

The following description relates to various embodiments for a high voltage (HV) connector for coupling an X-ray source to a source of high voltage electricity. The X-ray source may be included in an X-ray imaging system, an example block diagram of which is shown in FIG. 1. The X-ray imaging system may be an interventional radiography imaging system, a fluoroscopic imaging system, a mammography imaging system, a fixed or mobile radiography (RAD) imaging system, a tomographic imaging system, a computed tomography (CT) imaging system, and so on. The X-ray imaging system includes an X-ray source (e.g., an X-ray tube) to generate irradiating X-ray beams. A cross-sectional schematic view of an X-ray tube is shown in FIG. 2. The X-ray tube of FIG. 2 includes an anode assembly and a cathode assembly enclosed in an evacuated frame. The X-ray tube may be included in a C-arm interventional radiology or CT imaging system, as is shown in FIG. 3. The X-ray tube receives electric energy from an electrical power source, which, in some examples, may be a high voltage generator arranged at a substantial distance from the X-ray tube, a substantial distance meaning that the HV generator may be stored on another floor, in another room, or both, relative to the X-ray tube.

Figure 4:
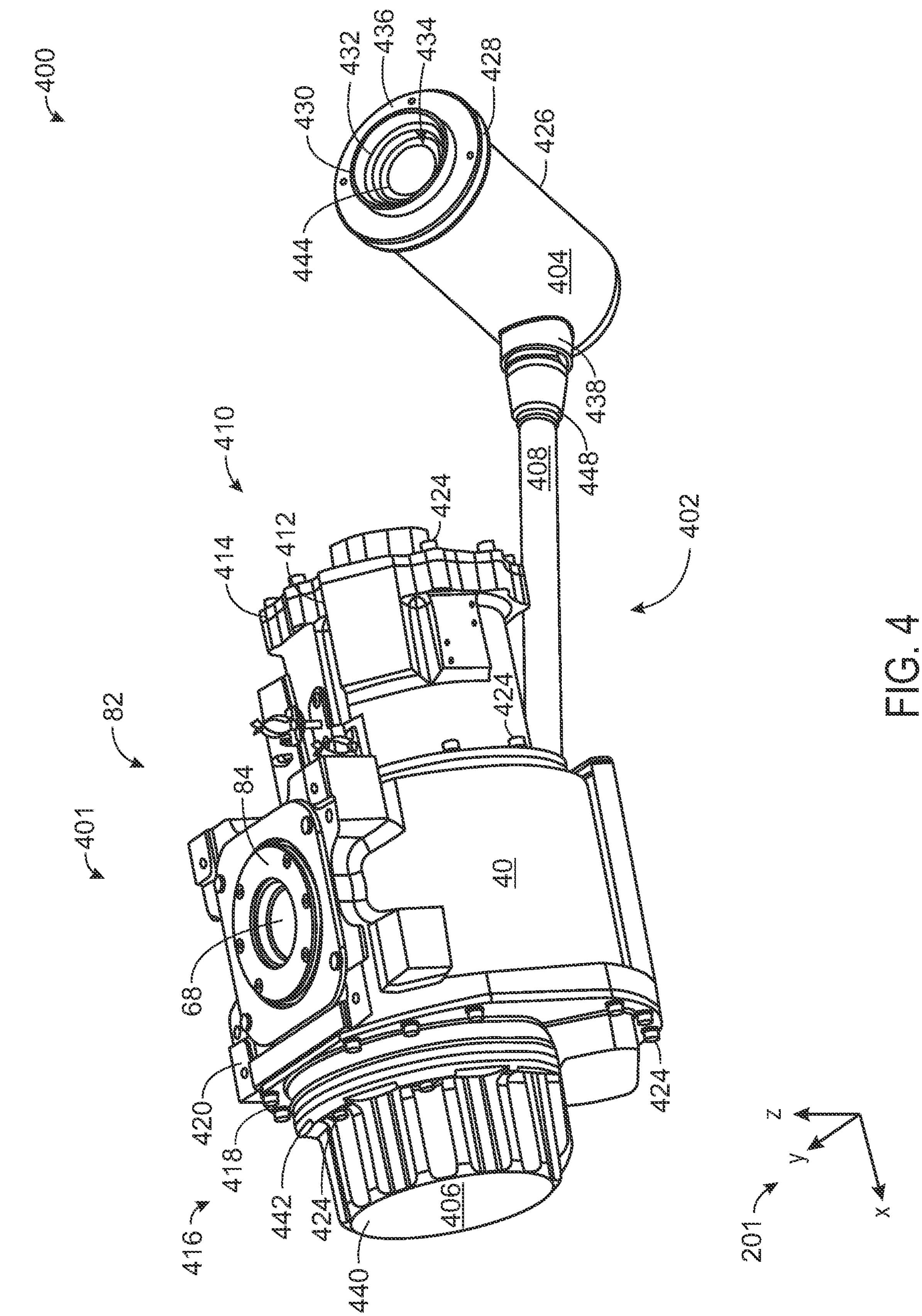
FIG. 4 shows a medical imaging assembly including an example of a high voltage connector of the present disclosure.
Figure 5A:
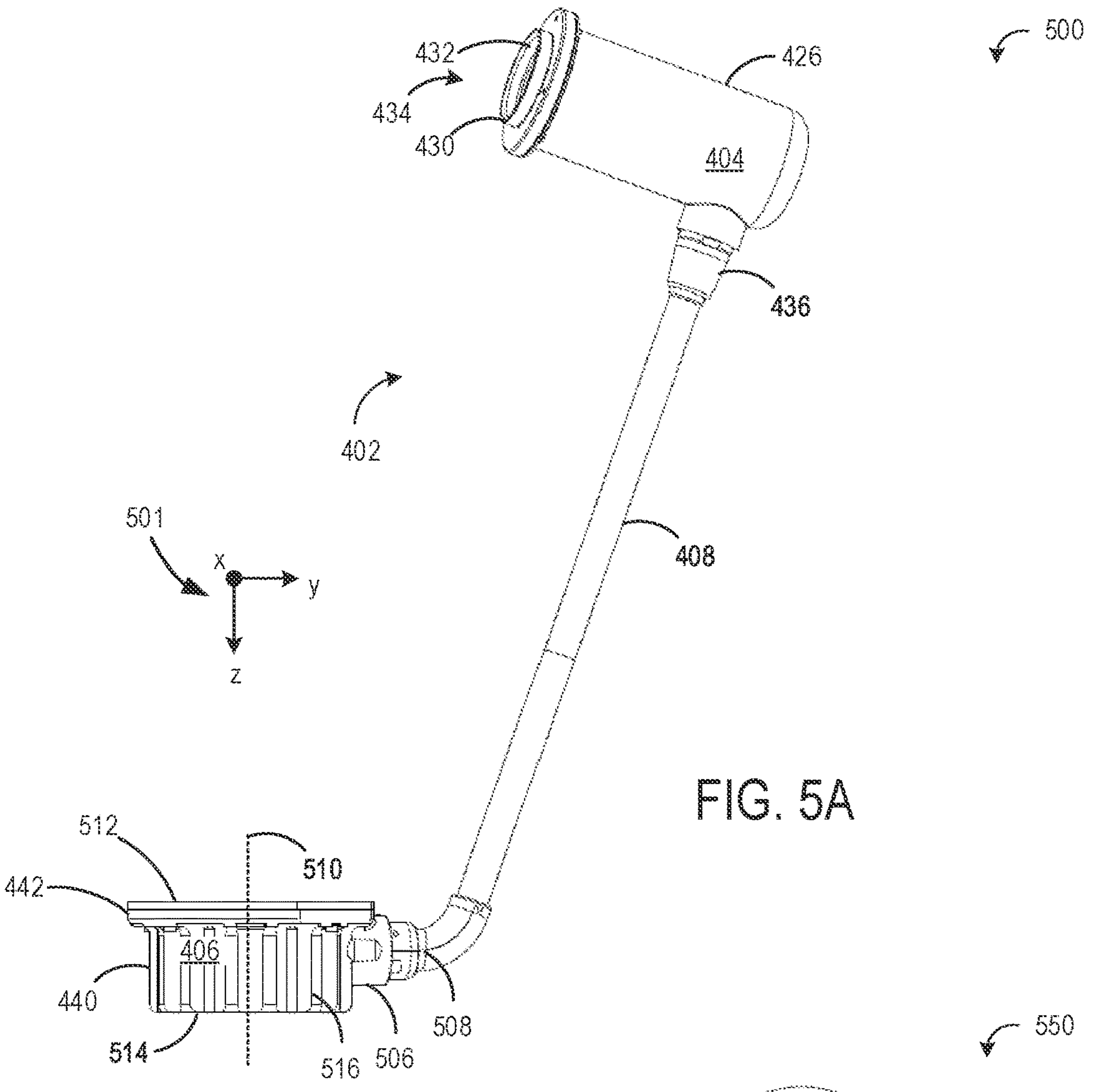
FIG. 5A shows a first perspective view of the high voltage connector of FIG. 4.
Figure 5B:
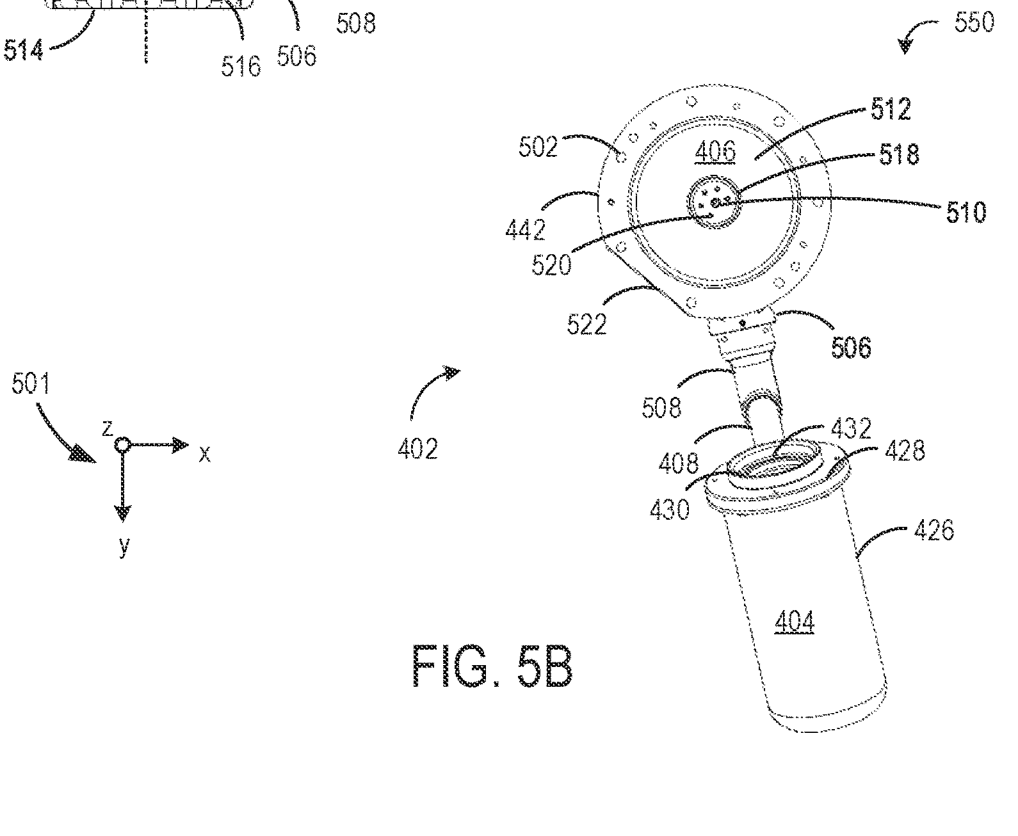
FIG. 5B shows a second perspective view of the high voltage connector of FIG. 4.
Figure 6:
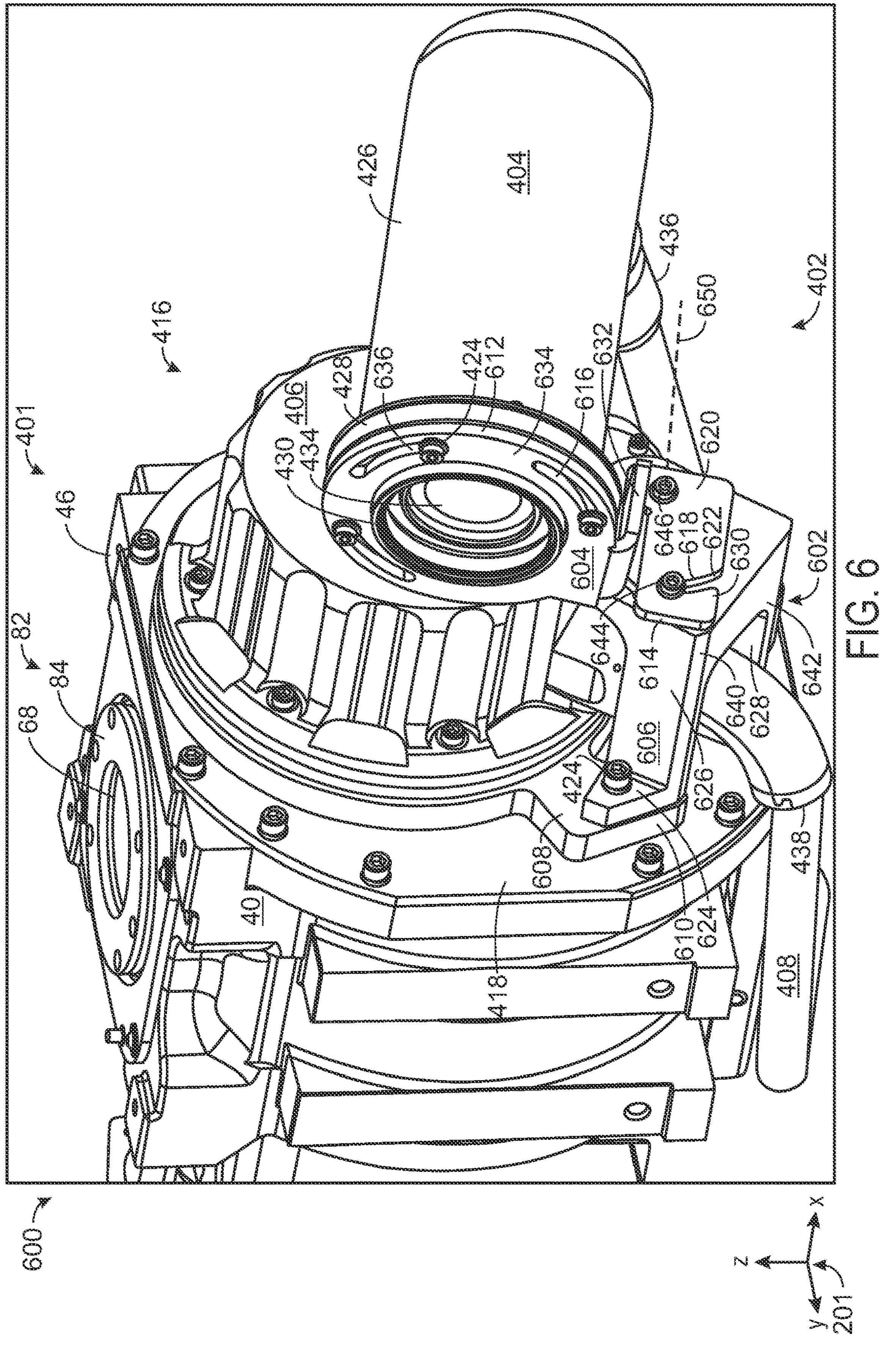
FIG. 6 shows a second perspective view of the medical imaging assembly of FIG. 4.
Figure 7:
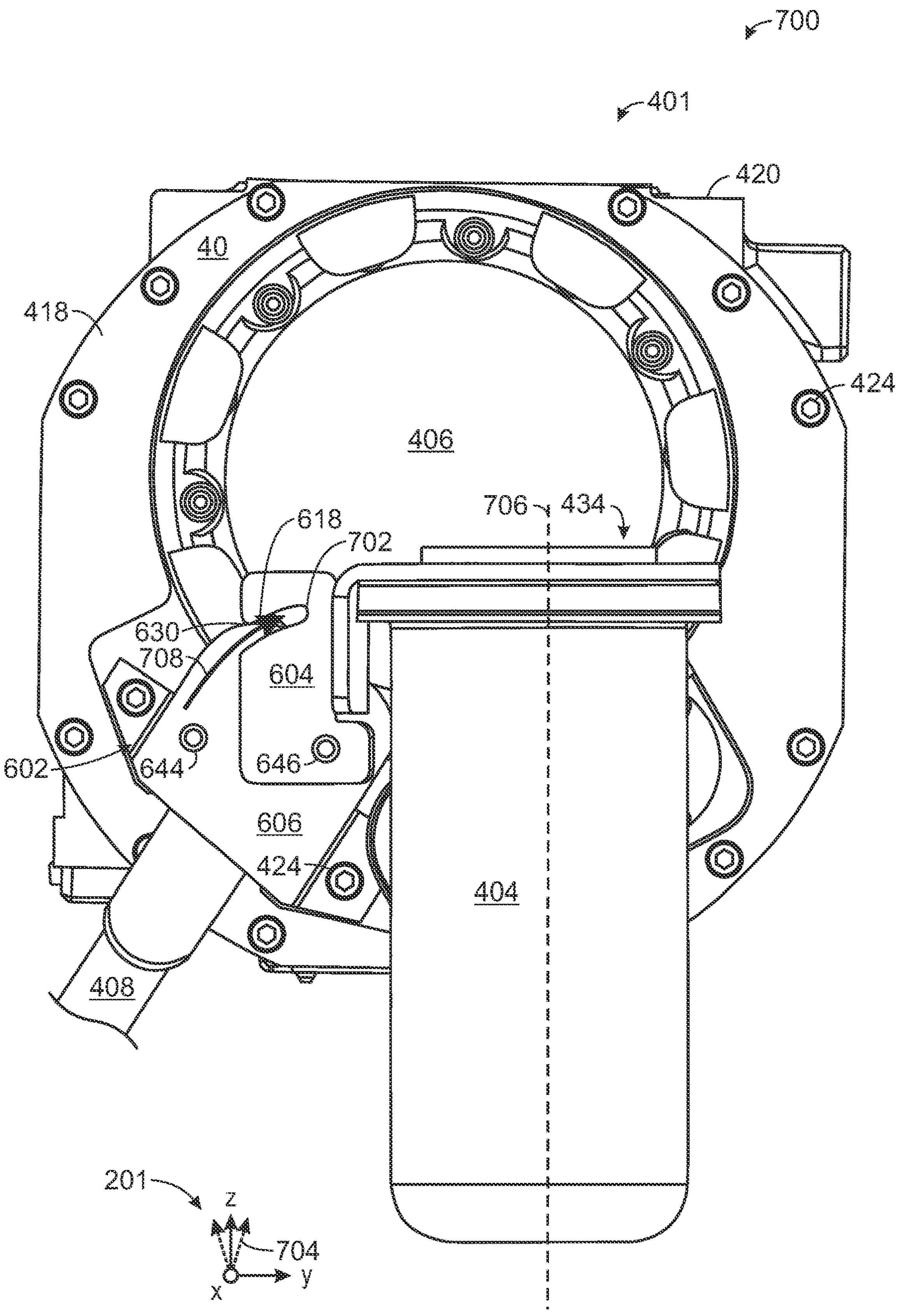
FIG. 7 shows an example of the medical imaging assembly of FIG. 4 with the generator side interface oriented in a first position for installation.
Figure 8:
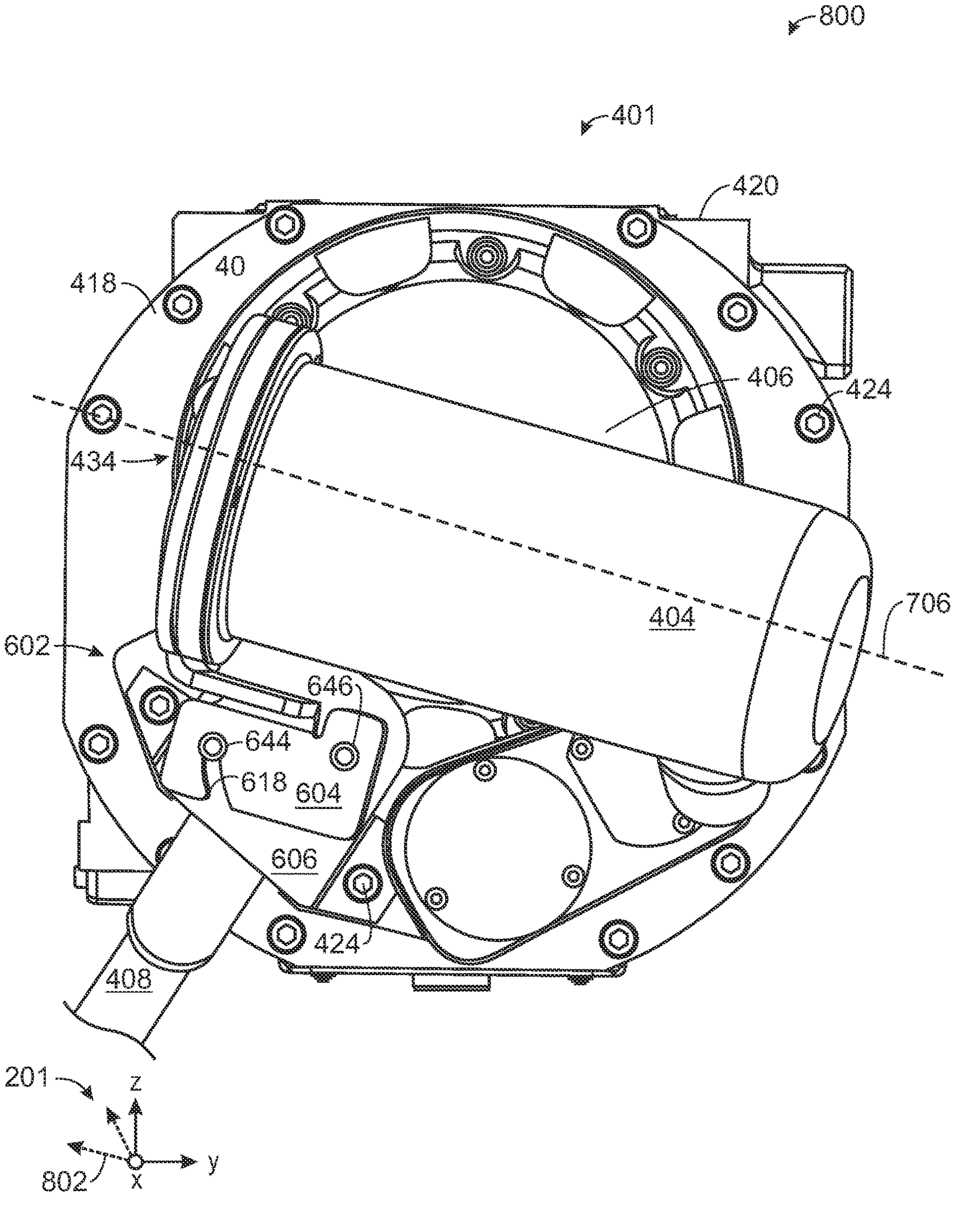
FIG. 8 shows an example of the medical imaging assembly of FIG. 4 with the generator side interface oriented in a second position for operation.
Figure 9:
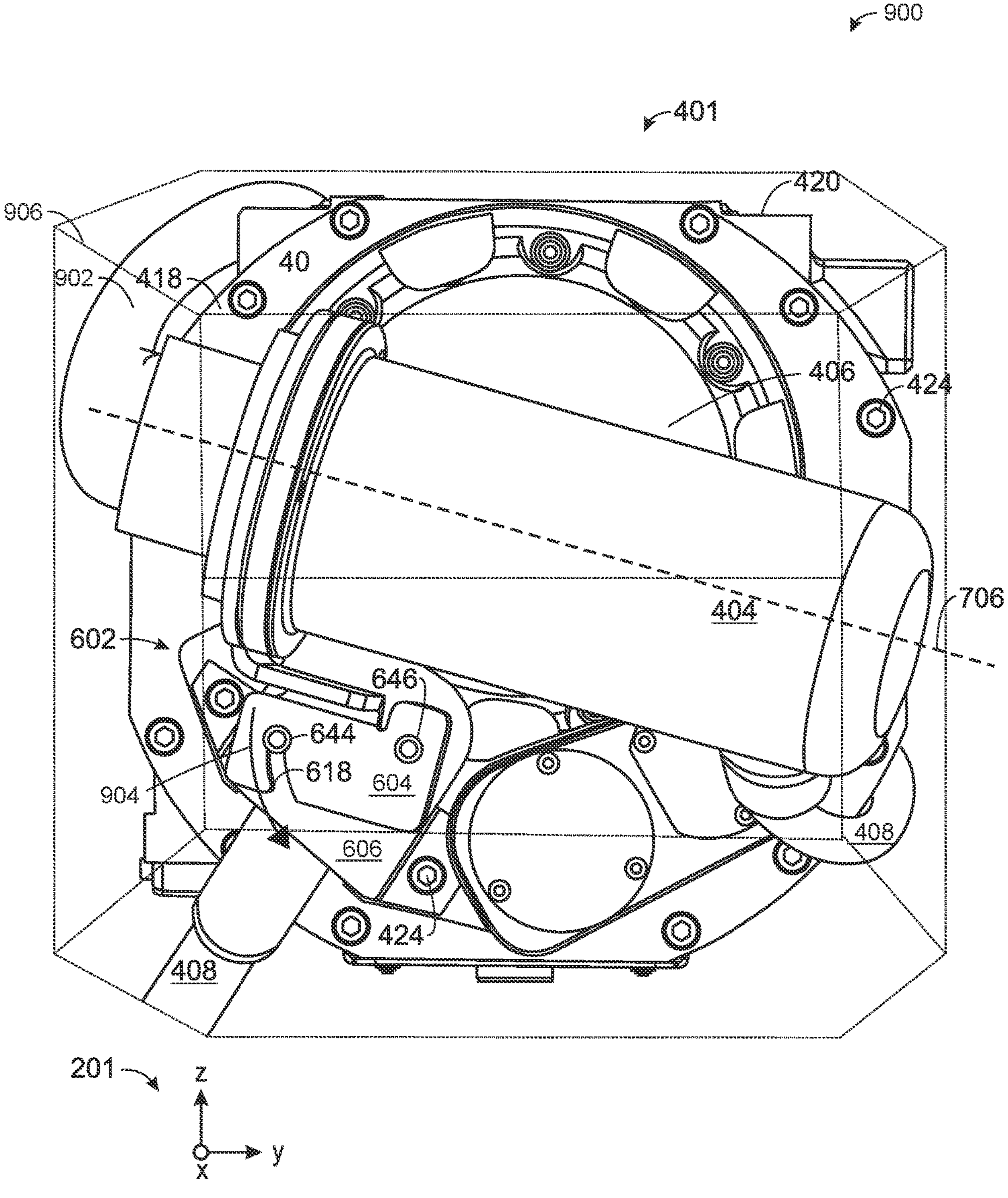
FIG. 9 shows an example of the medical imaging assembly of FIG. 4 coupled to a high voltage (HV) cable and enclosed in a housing for operation.
Figure 10:
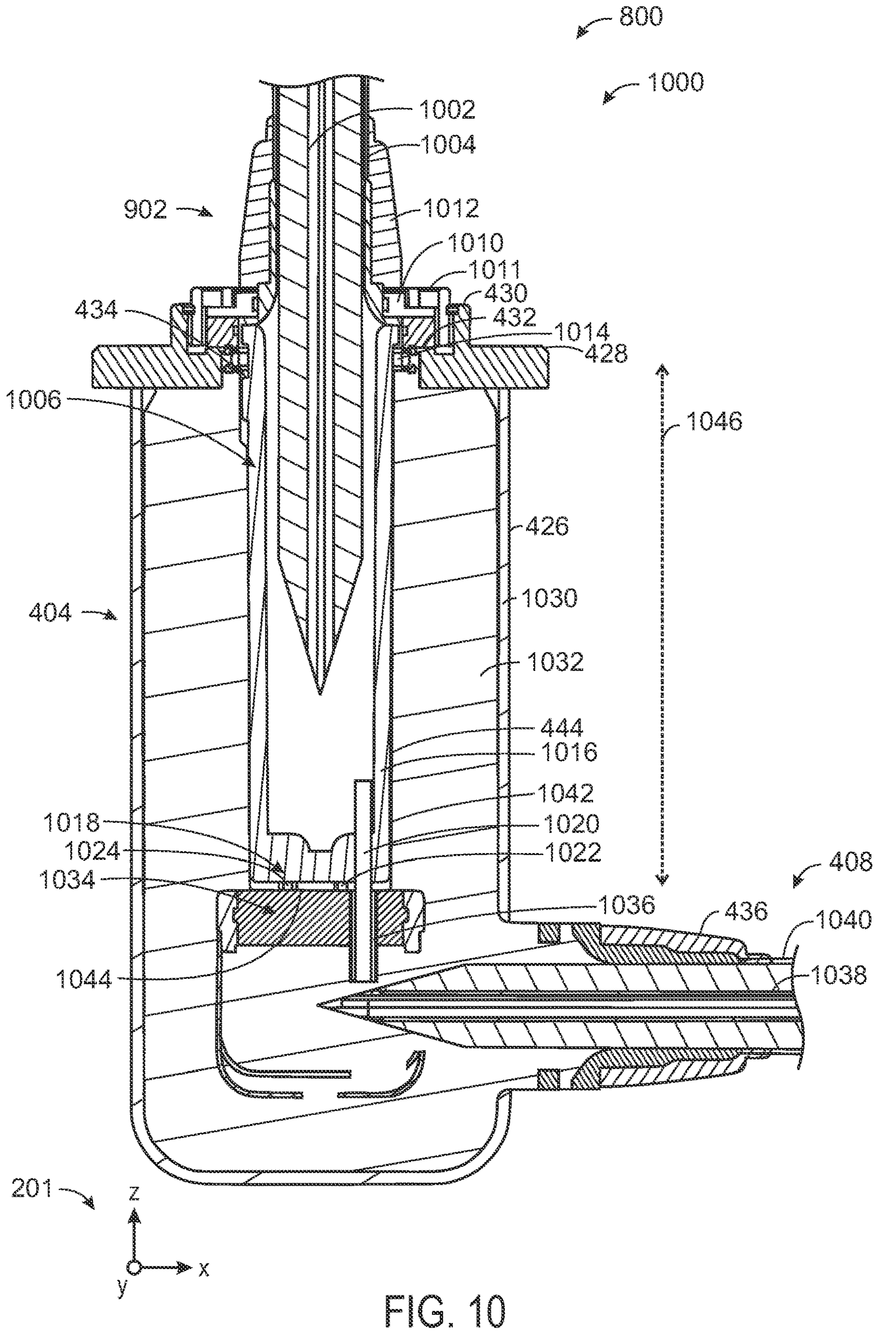
FIG. 10 shows a cross section of an HV cable coupled to a generator side interface of the present disclosure.

FIG. 4 shows a perspective view of a medical imaging assembly comprising an X-ray tube and a high voltage connector that is configured to couple the X-ray tube to a high voltage generator. The high voltage connector includes a generator side interface, an X-ray tube side interface, and an insulated conductor. The generator side interface includes a high voltage port that is configured to receive a mating electrical interface of a high voltage (HV) cable. The X-ray tube side interface may be mounted to a cathode side of the X-ray tube, electrically coupling to electrical leads supplying current and voltage to the cathode. Additional views of the high voltage connector are shown in FIG. 5A and FIG. 5B. The high voltage connector may include a bracket assembly that moveably couples the generator side interface to the cathode side of the X-ray tube. One example of a bracket assembly is shown in FIG. 6, including a first bracket coupled to the generator side interface, and a second bracket coupled to the X-ray tube casing and to the first bracket. FIG. 7 shows the generator side interface in a first position for installation and maintenance. FIG. 8 shows the generator side interface in a second position for operation of the X-ray tube. FIG. 9 shows a HV cable coupled to the medical imaging assembly of FIG. 4 and a medical device housing at least partially enclosing the medical imaging assembly. FIG. 10 shows a cross sectional view of the generator side interface including an oil envelope comprising a narrow volume between the mating electrical interface of the HV cable and inner surfaces of the HV port. FIGS. 4-10 are shown approximately to scale although other relative dimensions may be used. In one example, approximately may be understood as ±5%.

C-arm interventional radiology system or CT scanner systems may obtain X-ray images from a plurality of angles and positions by rotating around an imaging subject. C-arm interventional radiology systems or CT scanner systems may be configured to provide a range of imaging services including diagnostic applications and interventional applications. For example C-arm interventional radiology systems may be used for real-time imaging during surgeries, visualizing bone structures and injuries, guiding minimally invasive procedures, and in dentistry for oral surgery, endodontics, and orthodontics. C-arm interventional radiology system scanner systems generally comprise a C-arm, an X-ray tube and a detector assembly mounted to the C-arm, and a high voltage (HV) generator electrically coupled to the X-ray tube. Interventional systems usually have HV generators placed away from the patient due to space and noise constraints. This often results in routing the HV cables from another equipment room, and sometimes from another floor. The cables therefore may run tens of meters long. For example, an HV cable may be as many as 40 meters long and routed from an HV generator in equipment room through the C-arm to the X-ray tube. As the HV cables can get damaged/wear out during field use, the ability to replace HV cables with limited equipment downtime is desired.

Conventionally, C-arm interventional radiology system further comprise a HV connector that couples the HV cable to the X-ray tube. The HV connector may comprise a first terminal that may electrically couple to the X-ray tube, and an HV generator side interface that receives the HV cable. In some examples, an HV generator side interface may comprise a hollow receptacle or canister that receives a mating electrical interface of the HV cable. The HV cable installation and replacement generally includes disconnecting the HV cable from the HV connection interface of the X-ray tube, replacing the HV cable or degraded portion, filling/re-filling the receptacle or canister of the HV generator side interface with dielectric oil, and coupling the HV cable to the canister. In conventional systems, the HV connector, including the HV generator side interface, is fixed to the X-ray tube, often integral with a casing of the X-ray tube. The C-arm may be rotated for canister access and oil filling during installation or replacement.

However, challenges exist with next-generation C-arm interventional radiology system systems. For example, next-generation systems may be equipped with higher voltage and bias capabilities. As a result, the HV cable terminations are more sensitive to air bubble formation. Whereas lower voltage systems may tolerate small/few air bubble formation within the electrical interface, even small voids within the electrical interface of a high voltage system may cause high voltage stress, and may potentially degrade the HV connector, the HV cable, and other components of the C-arm interventional radiology system. For example, air bubbles in the mm to sub-mm size may be detrimental to HV insulation integrity particularly in applications where bias voltages in kV range exist in addition to main tube voltage of over 100 kV. This may also increase the risk of failures over time in systems when the C-arm is continuously re-oriented during field use.

Thus, a high voltage connector for a medical imaging system is disclosed herein to at least partly address the above-described issues. In one example, a high voltage connector for a medical imaging system comprises a generator side interface configured to couple to a high voltage generator, a tube side interface configured to couple to an X-ray tube, and an insulated conductor flexibly coupling the generator side interface to the tube side interface, wherein the generator side interface is positionable in an installation position and an operational position. In one example, the generator side interface comprises a high voltage port configured to receive a mating electrical interface of a high voltage generator cable. The tube side interface may comprise a flat cylindrical body including a plurality of electrical sockets configured to receive a plurality of electrical pins coupled to a cathode of the X-ray tube, and a substantially circular flange with a flat side formed by a segment offset from a central axis of the flange. The insulated conductor may comprise a flexible cable that bends to allow adjusting a position of the generator side interface relative to the tube side interface. In one example, the high voltage connector further comprises a bracket assembly comprising a first bracket configured to couple to the generator side interface, the first bracket comprising a slot, a second bracket configured to couple to an X-ray tube and to the first bracket, and a first fastener directly coupled to the second bracket and selectively directly coupled to the slot. In one example, the slot may comprise an open arc shape. In one example, the operational position comprises the first fastener directly coupled to the slot and the installation position comprises the first fastener free from direct contact with the slot. The ability of the bracket assembly and the insulated conductor to hold the receptacle in various orientations may increase operator control during installation and maintenance. For example, a maintenance operator may adjust the position of the generator side interface to increase access to the high voltage port. Further, by holding the generator side interface in a selected position, the bracket assembly allows a maintenance operator to use an expander wrench for tightening the seal between the mating interface of the HV cable and the canister.

The disclosed high voltage connector offers several advantages. The design allows for easy replacement of the HV cable, generator side interface, and tube side interface, reducing equipment downtime. The high voltage connector forms a compact tube/interface envelope, which may reduce the overall imaging equipment footprint and the user experience of the imaging equipment. The mounting bracket design and flexible connector accommodate multiple lockable receptacle orientations, which can be adjusted for maintenance, oil fill, or clinical use. Furthermore, the disclosed features may reduce equipment downtime when swapping cables and allow for a replaceable receptacle interface in case of tube side degradation. Overall, the disclosed features enhance the performance and longevity of the system. A technical advantage of the herein disclosed high voltage connector includes allowing higher X-ray tube voltage capability with reduced high voltage stress incidence by increasing the electrical stability between the high voltage generator and the X-ray tube by reducing the potential for air within the interface.

FIGS. 2-10 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example. Moreover, the components may be described as they relate to reference axes included in the drawings. As another example, features may be referred to as substantially shaped (e.g., such as being substantially circular, cylindrical, annular, straight, planar, curved, rounded, chamfered, angled, or the like), meaning the feature would be understood to be the shape by a person skilled in the art without being perfectly the shape.

Before further discussion of the high voltage connector for a medical imaging system, an example imaging system in which the high voltage connector may be implemented is shown. Turning now to FIG. 1, a block diagram is shown of an embodiment of an imaging system 10 configured both to acquire original image data and to process the image data for display and/or analysis in accordance with exemplary embodiments. It will be appreciated that various embodiments are applicable to numerous X-ray imaging systems implementing an X-ray tube, such as X-ray radiography (RAD) imaging systems, X-ray mammography imaging systems, fluoroscopic imaging systems, tomographic imaging systems, or CT imaging systems. The following discussion of the imaging system 10 is merely an example of one such implementation and is not intended to be limiting in terms of modality.

As shown in FIG. 1, imaging system 10 includes an X-ray device or X-ray source 12 configured to project a beam of X-rays 14 through an object 16. The object 16 may include a human subject, an animal subject, pieces of baggage, electronics, or other objects to be scanned. The X-ray source 12 may be next-generation X-ray tubes producing X-rays 14 having a spectrum of energies that range 70-140 keV. The X-rays 14 pass through the object 16 and, after being attenuated, impinge upon a detector assembly 18. Each detector module in the detector assembly 18 produces an analog electrical signal that represents the intensity of an impinging X-ray beam, and hence the attenuated beam, as it passes through the object 16. In one embodiment, detector assembly 18 is a scintillator based detector assembly, however, it is also envisioned that direct-conversion type detectors (e.g., CdTe, CZT, Si detectors, etc.) may also be implemented.

A processor 20 receives the signals from the detector assembly 18 and generates an image corresponding to the object 16 being scanned. A computer 22 communicates with the processor 20 to enable an operator, using an operator console 24, to control the scanning parameters and to view the generated image. That is, the operator console 24 includes some form of operator interface, such as a keyboard, mouse, voice activated controller, or any other suitable input apparatus that allows an operator to control the imaging system 10 and view the reconstructed image or other data from the computer 22 on a display unit 26. Additionally, the operator console 24 allows an operator to store the generated image in a storage device 28 that may include hard drives, floppy discs, compact discs, etc. The operator may also use the operator console 24 to provide commands and instructions to the computer 22 for controlling a source controller 30 that provides power and timing signals to the X-ray source 12.

FIG. 2 illustrates a cross-sectional schematic view of an X-ray device or X-ray source 200 that may be included in the imaging system of FIG. 1. For example, the X-ray source 200 may be an exemplary embodiment of the X-ray source 12 of FIG. 1, formed of an X-ray tube 40 that includes an anode assembly 42, a cathode assembly 44, and a collector assembly 82.

A set of reference axes 201 indicating an x-axis, a y-axis, and a z-axis are provided for comparison between views shown in FIG. 2 and following figures, (e.g., FIGS. 3-4, 6-10). The x-axis may be referred to as a lateral axis, the z-axis may be referred to as a vertical axis, and the y-axis may be referred to as a longitudinal axis. A direction of gravity may be opposite a positive direction of the z-axis. A filled circle may represent an arrow and axis facing toward a view. An unfilled circle may represent an arrow and an axis facing away from a view.

The X-ray tube 40 is supported by the anode assembly 42, the cathode assembly 44, and the collector assembly 82 within an envelope or frame 46, the frame housing at least a portion of the anode assembly 42, the cathode assembly 44, and the collector assembly 82. The frame 46 houses an anode 48 with a target 66, a bearing assembly 50, and a cathode 52. The frame 46 defines an area of relatively low pressure (e.g., a vacuum) compared to ambient, and in which high voltages may be present. Further, the frame 46 may be positioned within a casing (not shown) filled with a cooling medium, such as oil, that may also provide high voltage insulation. While the anode 48 configured with the target 66 is described above as being a common component of the X-ray tube 40, the anode 48 and target 66 may be separate components in alternative X-ray tube embodiments.

The cathode 52 receives one or more electrical signals via a series of electrical leads 56. The electrical leads 56 are coupled to an electrical power supply 90 via an electrical cable 92. Depending on the medical imaging application the electrical power supply 90 may be arranged at a substantial distance or within relative close proximity to the X-ray tube 40. In operation, an electron beam is produced by the cathode assembly 44. The electron beam occupies a space 54 between the cathode 52 and the target 66 of the anode 48. The electrical signals may be timing/control signals that cause the cathode 52 to emit the electron beam at one or more energies and at one or more frequencies. The electrical signals may also at least partially control the potential between the cathode 52 and the anode 48. Cathode 52 includes a central insulating shell 58 from which a mask 60 extends. Mask 60 encloses the electrical leads 56, which extend to a cathode cup 62 mounted at the end of mask 60. In some examples, the cathode cup 62 serves as an electrostatic lens that focuses electrons emitted from a filament within the cathode cup 62 to form the electron beam.

X-rays 64 are produced when high-speed electrons of the electron beam are suddenly decelerated when directed from the cathode 52 to the target 66 formed on the anode 48 via a potential difference therebetween of, for example, sixty thousand (60,000) volts or more in the case of CT applications. The collector assembly 82 may include an electron collector 84 and a window 68, through which X-rays 64 generated by the anode assembly 42 are emitted. The electron collector 84 may hold the window 68 in place in the frame 46 and may further absorb backscatter electrons. The X-rays 64 are emitted through window 68 formed in the frame 46 toward a detector array, such as the detector assembly 18 of FIG. 1.

Anode assembly 42 includes a rotor 72 and a stator (not shown) located outside the X-ray tube 40 and surrounding the rotor 72 for causing rotation of the anode 48 during operation. The anode 48 is supported for rotation by a bearing arm or a bearing assembly 50, which, when rotated, also causes the anode 48 to rotate about a centerline 70 thereof. As such, the centerline 70 defines a rotational axis of the anode 48 and the bearing assembly 50. As shown, the anode 48 has an annular shape, which contains a circular opening 74 in the center thereof for receiving the bearing assembly 50.

The anode 48 may be manufactured to include a number of metals or alloys, such as tungsten, molybdenum, copper, or any material that contributes to bremsstrahlung (e.g., deceleration radiation) when bombarded with electrons. The target 66 of the anode 48 may be selected to have a relatively high refractory value so as to withstand the heat generated by electrons impacting the anode 48. Further, the space between the cathode assembly 44 and the anode 48 may be evacuated in order to minimize electron collisions with other atoms and to maximize an electric potential.

To avoid overheating of the anode 48 when bombarded by the electrons, the rotor 72 rotates the anode 48 at a high rate of speed (e.g., 90 to 250 Hz) about the centerline 70. In addition to the rotation of the anode 48 within the frame 46, in a CT application, the X-ray tube 40 as a whole is caused to rotate about an object, such as the object 16 of the imaging system 10 in FIG. 1, at rates of typically 1 Hz or faster.

Different embodiments of the bearing assembly 50 may be formed, such as with a number of suitable ball bearings, but in the illustrated exemplary embodiment comprises a liquid metal hydrodynamic bearing having adequate load-bearing capability and acceptable acoustic noise levels for operation within the imaging system 10 of FIG. 1.

In general, the bearing assembly 50 includes a stationary component, such as a center shaft 76, and a rotating portion, such as a sleeve 78 to which the anode 48 is attached. While the center shaft 76 is described with respect to FIG. 2 as the stationary component of the bearing assembly 50 and the sleeve 78 is described as the rotating component of the bearing assembly 50, embodiments of the present disclosure are also applicable to embodiments wherein the center shaft 76 is a rotary shaft and the sleeve 78 is a stationary component. In such a configuration, the anode 48 may rotate as the center shaft 76 rotates.

The center shaft 76 may optionally include a cavity or coolant flow path 80 through which a coolant (not shown), such as oil, may flow to cool the bearing assembly 50. As such, the coolant enables heat generated from the anode 48 of the X-ray tube 40 to be extracted therefrom and transferred external from the X-ray tube 40. In straddle mounted X-ray tube configurations, the coolant flow path 80 extends along a longitudinal length of the X-ray tube 40, e.g., along the centerline 70. In alternative embodiments, the coolant flow path 80 may extend through only a portion of the X-ray tube 40, such as in configurations where the X-ray tube 40 is cantilevered when placed in an imaging system.

The X-ray tube of FIG. 2 includes an anode assembly and a cathode assembly enclosed in an evacuated frame. The X-ray tube may be included in a C-arm interventional radiology system, as is shown in FIG. 3. The X-ray tube receives electric energy from an electrical power source, which, in some examples, may be high voltage generator arranged at a substantial distance from the X-ray tube. For example, a substantial distance may mean the HV generator is stored on another floor, in another room, or both, relative to the X-ray tube.

FIG. 3 shows a pictorial diagram of a C-arm interventional radiology system, hereinafter a C-arm system 300. The C-arm system 300 may be an exemplary embodiment of the imaging system 10 of FIG. 1. The C-arm system 300 includes a high voltage (HV) generator 302, a medical imaging device 304, and the X-ray tube 40 of FIG. 2 electrically coupled to the HV generator 302 and mounted to the medical imaging device 304. A high voltage generator cable, hereinafter an HV cable 312, conducts a flow of electric current from the HV generator 302 to the X-ray tube 40. In one example, the X-ray tube 40 may be a monopolar X-ray tube. A detector 314 is mounted to the medical imaging device 304. The detector 314 may be an exemplary embodiment of the detector assembly 18 of FIG. 1.

The medical imaging device 304 may be an example of a C-arm interventional radiology system. In some applications, such as shown in FIG. 3, the high voltage generator may be arranged in a first location and the C-arm interventional radiology system in a second location, where the first location is a substantial distance from second location. For example, in the case of interventional applications, which may use the medical imaging device for precision guiding and placement of a probe or needle, arranging the HV generator at a distance from the medical imaging device may save valuable space in a procedure room, and may reduce noise and electromagnetic interference by the HV generator. In one example, the HV generator 302 is arranged on a second floor equipment room, which is separate and spaced apart from, a first floor procedure room where the medical imaging device 304 is operated. The HV cable 312 may be fed through one or more of a structure or feature, such as a wall, a ceiling, a floor, etc. The HV cable 312 may be electrically coupled to the X-ray tube 40 of the medical imaging device 304. For example, the HV cable 312 may extend 10-40 meters, or more, from the HV generator 302 to the medical imaging device 304.

The medical imaging device 304 includes a C-arm 306, a base 308, and an L-arm 320 coupling the C-arm 306 to the base 308. The C-arm 306, the base 308, and the L-arm 320 may comprise housings that enclose electrical and mechanical components of the medical imaging device 304. For example, the HV cable 312 enters the medical imaging device 304 at the base 308, is fed through the L-arm 320, and coupled to the X-ray tube 40. Similarly, electromechanical components (not shown), which may be operated to control a position of the X-ray tube 40, may be enclosed within one or more of the C-arm 306, the L-arm 320, and the base 308.

The X-ray tube 40 and the detector 314 are coupled to the C-arm 306. The C-arm 306 may be controlled to rotate the X-ray tube 40 and the detector 314. For example, the C-arm 306 may be controlled to rotate the X-ray tube 40 and the detector 314 around the y-axis along a path 316. As another example, the C-arm 306 may be controlled to rotate the X-ray tube 40 and the detector 314 around the x-axis. In other examples, the C-arm 306 may be controlled to rotate in other directions. A display 322 and an examination table 324 may be arranged in proximity of the medical imaging device 304. An operator may control the position of the C-arm 306 to obtain medical images of a subject resting on the examination table 324. For example, an operator may rotate or otherwise adjust the position of C-arm 306 to image the subject from a variety of angles and distances. In some examples, the operator may control the position of the C-arm 306, and the X-ray tube 40 and detector 314 coupled thereon, based on real-time images of the subject that are generated on the display 322. As another example, the operator may conduct a medical procedure based on real-time images generated via the display 322.

FIG. 4 shows a perspective view 400 of a medical imaging assembly 401 including an exemplary embodiment of the X-ray tube 40 coupled to a high voltage connector, hereinafter an HV connector 402. The HV connector 402 is configured to couple the X-ray tube 40 to a high voltage generator, such as the HV generator 302 of FIG. 3. The HV connector 402 includes an HV generator side interface, hereinafter a generator side interface 404, an X-ray tube side interface, hereinafter a tube side interface 406, and an insulated conductor 408. Elements of the medical imaging assembly 401 that are equivalent to elements of the X-ray tube 40 of FIG. 2 are similarly numbered and not reintroduced.

The medical imaging assembly 401 includes a cathode end 416, which may describe the end of the X-ray tube 40 relative to the cathode assembly 44 (in FIG. 2) enclosed therein, and an anode end 410, which may describe the end of the X-ray tube 40 relative to the anode 48 (in FIG. 2) enclosed therein. The X-ray tube 40 includes a casing comprising an anode end piece 412 and an anode end plate 414 arranged on the anode end 410, a central piece 420, and a cathode end plate 418 arranged on the cathode end 416. The cathode end plate 418 and the anode end piece 412 are coupled to the central piece 420 via a plurality of fasteners 424 (e.g., bolts, rivets, etc.). The anode end plate 414 is coupled to the anode end piece 412 similarly with fasteners 424.

The generator side interface 404 may comprise a hollow receptacle or canister configured to receive a mating electrical interface of a high voltage generator cable, such as the HV cable 312 of FIG. 3. The generator side interface 404 may include a canister body 426 and a canister cap 428 positioned on an upper end of the canister body 426. In one example, the canister body 426 may be substantially cylindrical shaped and the canister cap 428 may be substantially annulus shaped. In other examples, the canister body 426 may include various forms and shapes depending on available space. The canister cap 428 may include a canister cap face 436, a lip 430, and a seat 432 forming a perimeter around a recess, herein a high voltage port or HV port 434. The seat 432 abuts the HV port 434. In one example, the HV port 434 comprises an inner cylindrical surface 444. The HV port 434 is configured to receive the mating electrical interface of the HV cable. For example, the HV port 434 may be configured to receive a plug having a plurality of contact pins, such as a custom federal standard termination (e.g., see FIG. 9). The generator side interface 404 may include a second port 438 where the insulated conductor 408 electrically couples to the canister body 426.

The tube side interface 406 is coupled to the X-ray tube 40 on the cathode end 416, electrically coupling to the electrical leads 56 (in FIG. 2) supplying current to the cathode assembly 44. In one example, the tube side interface 406 comprises a substantially cylindrical member 440 and a flange 442. A plurality of fasteners 424 inserted through a plurality of through holes 504 (see FIGS. 5A-B) in the flange 442 may couple the tube side interface 406 to the cathode end plate 418. The tube side interface 406 may include a third port 506 (see FIGS. 5A-B) where the insulated conductor 408 electrically couples to the substantially cylindrical member 440. In one example, the tube side interface 406 may comprise a short cylinder or "pancake" shape. For example, a short cylinder or "pancake" shape may be a typical configuration when the HV interface is not encased in oil medium. However, in other examples the tube side interface 406 may be various shapes as long as compressive uniform loading over the interface is achieved.

In one example, the insulated conductor 408 may comprise a flexible cable which bends to allow the generator side interface 404 to be positioned in various orientations relative to the tube side interface 406. In the view shown, the insulated conductor 408 is extended, thereby positioning the generator side interface 404 nearer the anode end 410. However, it may be understood that in other examples, such as when installed in a housing of a medical imaging device and as shown in subsequent figures, the insulated conductor 408 may bend to position the generator side interface 404 nearer the cathode end 416. The insulated conductor 408 may include a first end cap 448 that protects and seals the electrical interface with the generator side interface 404 at the second port 438. The insulated conductor 408 may include a second end cap 508 (see FIGS. 5A-B) that protects and seals the electrical interface with the tube side interface 406 at the third port 506.

FIGS. 5A-B are additional views 500 and 550 of the HV connector 402 of FIG. 4 isolated from the X-ray tube 40. Elements of the medical imaging assembly 401 introduced with reference to FIG. 4 are similarly numbered and not reintroduced. Elements previously introduced but not shown in FIG. 4 include the plurality of through holes 502 arranged in the flange 442 of the tube side interface 406, the third port 506 of the tube side interface 406, and second end cap 508 of the insulated conductor 408. A set of reference axes 501 indicating an x-axis, a y-axis, and a z-axis are provided for comparison between additional views 500 and 550.

As shown in view 500, the tube side interface 406 may include a first face 512 arranged in parallel with a second face 514. A central axis 510 of the tube side interface 406 passes through the centers of the first and second faces 512, 514 and the center of the substantially cylindrical member 440. The substantially cylindrical member 440 may include a ribbed outer casing 516.

As shown in view 550, the flange 442 may comprise a substantially circular member with a flat side 522 formed by a segment (e.g., a slice, a cut) offset from the central axis 510 (shown as a hollow circle). The tube side interface 406 may further include a terminal 518 comprising a plurality of electrical sockets 520 configured to receive a plurality of electrical pins coupled to a cathode of an X-ray tube, such as X-ray tube 40. In one example, the plurality of electrical sockets 520 may be arranged in proximity of the central axis 510.

FIG. 6 shows a perspective view 600 of the medical imaging assembly 401 including an exemplary embodiment a bracket assembly 602 movably coupling the generator side interface 404 to the cathode end 416 of the X-ray tube 40. In one example, the bracket assembly 602 comprises a first bracket 604 coupled to the generator side interface 404, the first bracket comprising a slot 618, and a second bracket 606 coupled to the X-ray tube and to the first bracket 604. The bracket assembly 602 further comprises a first fastener 644 directly coupled to the second bracket 606 and selectively directly coupled to the slot 618. Elements of the medical imaging assembly 401 introduced with reference to FIGS. 4-5B are similarly numbered and not reintroduced.

The first bracket 604 may comprise a flange 612, a tab 614, and a folded element 632 interposed between the flange 612 and the tab 614. The flange 612 may be annulus shaped comprising a first bracket face 634 and a rear face (not shown) in face sharing contact with the canister cap 428. A plurality of through holes 616 are arranged around a perimeter of the flange 612. In one example, the plurality of through holes 616 comprise elongate through holes, each defined by an arc shaped opening on the first bracket face 634, an opening on the rear face, and through-hole surface 636. Fasteners (e.g., of the plurality of fasteners 424) inserted through each of the through holes 616 may couple the flange 612 to the canister cap 428. In one example, the elongate shape of the holes 616 helps to locate the canister cap face 436 with respect to the X-ray tube 40 and allows for the canister cap face 436 to 'get out of the way' when rotating the generator side interface 404 to the vertical position. The tab 614 includes a tab face 620, a rear face (not shown) in face sharing contact with the second bracket 606, and the slot 618. In one example, the slot 618 may be defined by an arc shaped cutaway in the tab face 620, an arc shaped cutaway on the rear face of the tab 614, and a slot surface 622. The slot 618 may comprise an open arc shape with a closed end 702 (see FIG. 7) and an open end 630.

The second bracket 606 may comprise a body 640. The body 640 may include a first leg 626 with a first foot 624, a second leg 628 with a second foot (not shown), and a platform 642 interposed between and arranged perpendicular to the first leg 626 and the second leg 628. In one example, the first foot 624 and the second foot (not shown) are directly coupled to a face 610 of a raised portion 608 of the cathode end plate 418.

The generator side interface 404 may be mounted to the X-ray tube 40 but can be rotated to hold the HV port 434 in a vertical position. In one example, the rotational freedom is accomplished by a pair of fasteners coupling the first bracket 604 to the second bracket 606. In one example, a second fastener 646 may directly couple the tab 614 to the platform 642 and the first fastener 644 may selectively and directly couple to the slot 618. In one example, the tab 614 may pivot around a rotational axis 650 of the second fastener 646. The slot 618 may directly couple to the first fastener 644 during some conditions, such as when the generator side interface 404 is positioned for operation, and may not during other conditions, such as when the generator side interface 404 is positioned for installation, maintenance, oil filling, etc.

In the example shown in FIG. 6, the bracket assembly 602 includes the first bracket 604 and the second bracket 606. However, in other examples, the bracket assembly may include a single bracket that accomplishes the pivoting function of the bracket assembly. For example, the single bracket may rotatably couple the generator side interface 404 directly to the cathode end plate 418 or the raised portion 608. As one example, there may be a single, moveable bracket. The single, movable bracket may be positioned in a like position or another functional position to enable the rotatable coupling. Additionally, or alternatively, the single, moveable bracket may be sized similarly. In another example, the bracket assembly may include more than two brackets, such as three brackets, which coordinate to accomplish the pivoting function and may be similarly sized and/or similarly positioned.

FIG. 7 shows an example of the medical imaging assembly 401 with the generator side interface 404 oriented in an installation position 700. Elements of the medical imaging assembly 401 introduced with reference to FIGS. 4-6 are similarly numbered and not reintroduced.

In one example, the installation position 700 may comprise the HV port 434 facing upward (e.g., the recess pointing up), and a central axis 706 of the HV port 434 oriented in a positive vertical position within a first threshold range. In the example, the vertical axis is indicated by the z-axis. In other words, the installation position 700 may include the HV port 434 arranged opposite from the direction of gravity. The first threshold range may be a positive, non-zero threshold range. As one example, the installation position 700 may comprise the generator side interface 404 oriented in a vertical position ±10°, as indicated by dotted arrows 704 (e.g., between +75° and 105° relative to the horizontal axis). In other examples, the installation position 700 may comprise the generator side interface 404 oriented in a vertical position ±5°, +15°, or another range. In the example, the installation position 700 includes the first fastener 644 free from direct contact with the slot 618.

In one example, during an installation or maintenance procedure, a maintenance operator may rotate the generator side interface 404 in a direction indicated by an arrow 708 to a selected position within the first threshold range. The bracket assembly 602 may hold the generator side interface 404 in the selected position. In other words, the generator side interface 404 may remain in the selected position without manual assistance (e.g., lockingly) until the maintenance operator adjusts the position. With the generator side interface 404 supported by the bracket assembly 602, the maintenance operator may insert, remove, or otherwise adjust the mechanical and/or electrical connection between with the generator side interface 404 and an HV cable, such as the HV cable 312. Further, the maintenance operator may fill/refill the HV port 434 with dielectric oil. The installation position 700 may additionally increase access to other parts of the medical imaging assembly 401, such as the second port 438, the tube side interface 406, the insulated conductor 408, the first end cap 448, the second end cap 508, and so on. In one example, by holding the generator side interface 404 in a selected position, the bracket assembly 602 may allow the maintenance operator to tighten the seal between the mating electrical interface of the HV cable and the generator side interface 404 using one hand, such as with an expander wrench, for increased efficiency.

FIG. 8 shows an example of the medical imaging assembly 401 with the generator side interface 404 oriented in an operational position 800. Elements of the medical imaging assembly 401 introduced with reference to FIGS. 4-7 are similarly numbered and not reintroduced.

In one example, the operational position 800 may comprise the first fastener 644 directly coupled to the slot 618. In one example, directly coupled to the slot 618 may comprise a position anywhere along the length of the slot 618 (e.g., between the closed end 702 and the open end 630 in FIG. 7), where the first fastener 644 makes direct contact with the slot surface 622. Additionally, or alternatively, the operational position 800 may comprise the central axis 706 of the generator side interface 404 oriented in a horizontal position within a second threshold range. In the example, the y-axis is the horizontal axis. The second threshold range may be a positive, non-zero threshold range. In one example, the second threshold range is indicated by dotted arrows 802. For example, the operational position 800 may comprise the central axis 706 oriented +10° to +50° relative to the horizontal axis. In other examples, the operational position 800 may comprise the generator side interface 404 oriented +5° to +55°, 15° to +40°, or another range, relative to the horizontal axis.

FIG. 9 shows a second example 900 of the medical imaging assembly 401 with the generator side interface 404 oriented in an operational position. Elements of the medical imaging assembly 401 introduced with reference to FIGS. 4-8 are similarly numbered and not reintroduced.

In some examples, the operational position may include the generator side interface oriented within the second threshold range relative to the horizontal axis (e.g., dotted arrows 802 in FIG. 8), and may further include an HV cable electrically coupled to the generator side interface, and a housing of the medical device enclosed over the X-ray tube assembly. For example, during an installation or maintenance procedure, following oil filling, the maintenance operator may secure an HV cable 902 to the generator side interface 404. The HV cable 902 may extend to an HV generator, e.g., HV generator 302 in FIG. 3. The maintenance operator may rotate the generator side interface 404 to the operational position in a direction indicated by the arrow 904. The bracket assembly 602 may hold the generator side interface 404 in the operational position. The maintenance operator may tighten the first fastener 644 and/or the second fastener 646 to secure the position of generator side interface 404 in the operational position, and enclose a housing 906 (shown schematically) of the medical device around medical imaging assembly 401. The medical imaging assembly 401 comprises a compact footprint when installed and enclosed in the housing 906.

FIG. 10 shows a cross sectional detail view 1000 of a portion of the medical imaging assembly 401. The view includes the generator side interface 404 coupled to the HV cable 902. In one example the HV cable 902 may be the same as the HV cable 312 described with reference to FIG. 3. In one example, the HV cable 902 may be the same type of cable as the HV cable 312 described with reference to FIG. 3. Elements of the medical imaging assembly 401 introduced with reference to FIGS. 4-9 are similarly numbered and not reintroduced.

The HV cable 902 includes a plurality of conductors 1002 (e.g., wires) enclosed by an insulating layer 1004, a collar 1010, an end cap 1012, and a plug 1006 arranged below the collar 1010. The end cap 1012 surrounds the insulating layer 1004 at the interface between the collar 1010 and the canister cap 428. The collar 1010 may sit on the seat 432 in contact with the lip 430 of the canister cap 428. A gasket 1014 may be interposed between the collar 1010, the canister cap 428, and the plug 1006, sealing the interfaces there between. The collar 1010 may be fastened to the canister cap 428 via plurality of fasteners 1011.

The plug 1006 may include a housing 1016. The plurality of conductors 1002 extend through the housing 1016 to a termination 1018. The termination 1018 may include a first plurality of conductive elements. For example, a first contact pin 1020, a second contact pin 1022, and a third contact pin 1024 are shown in the cross sectional detail view 1000. In one example, the termination 1018 may comprise two additional contact pins (not shown). For example, the plurality of conductors 1002 may comprise five conductors and the plug 1006 may comprise a five pin version of a federal standard termination. In some examples, there may be more or fewer conductive elements comprising the termination of the plug of the HV cable. In one example, a federal standard or NEMA standard HV termination refers to a similar geometry with three contacts. The disclosed examples may include a modified version of the NEMA standard including five contacts.

The generator side interface 404 includes the canister body 426, which may further include a canister casing 1030 surrounding an insulating layer 1032. The insulating layer 1032 may include the inner cylindrical surface 444 that forms the HV port 434. In some examples, the inner cylindrical surface 444 is coated with epoxy. A canister termination 1034 may be arranged at a base 1044 of the HV port 434. The canister termination 1034 may include a second plurality of conductive elements. For example, a first socket 1036 is shown in the cross sectional detail view 1000. In one example, the canister termination 1034 may comprise four additional sockets, which interface with the first plurality of conductive elements. In one example, the first plurality of conductive elements are inserted into the second plurality of conductive elements. For example, the first contact pin 1020 may be inserted into the first socket 1036 to establish an electrical connection.

The insulated conductor 408 may include a plurality of conductors 1038 enclosed by an insulating layer 1040. The insulating layer 1040 may comprise a flexible material such as PVC plastic, fluoropolymer, rubber, cross-linked polyethylene or another suitable material. The plurality of conductors 1038 may extend into the generator side interface 404 via the second port 438, where the plurality of conductors 1038 may electrically couple to the canister termination 1034.

In some examples, the plug 1006 may comprise a candlestick shape, which complements the shape of the recess comprising the HV port 434. When electrically coupled, as is shown in FIG. 10, the plug 1006 substantially fills the HV port 434. An oil envelope 1042 comprises a narrow volume between the plug 1006 of the HV cable 902 and the inner cylindrical surface 444 of the HV port 434. The oil envelope 1042 runs the entire length of the interface, shown by double-headed arrow 1046, between the HV port 434 and plug 1006 from the base 1044 to gasket 1014. The oil envelope 1042 may include visibly more clearance at the base 1044 where the contact pins 1020, 1022, 1024 of the plug 1006 interface with the first socket 1036 (and others not shown) of the HV port 434.

During installation and maintenance, dielectric oil or alternative dielectric liquid or gel is added to the HV port 434 to fill the oil envelope 1042. For X-ray device operation, it is preferred to fill the oil envelope 1042 sufficiently and without any air pockets. As previously noted, air pockets may become high voltage stress points, which are a particular challenge for higher voltage, next-generation X-ray devices, such as the exemplary C-arm system 300 described herein. For example, even small pockets of air may cause issues during X-ray operation due to the rotation of the C-arm. The flexibility of the insulated conductor 408, and the bracket assembly 602 (e.g., see FIGS. 6-9) offer the freedom to orient the HV port 434 during installation and maintenance to ensure sufficient filling of the oil envelope 1042 and proper sealing of the collar 1010 and the canister cap 428.

In this way, by providing multiple lockable canister orientations, which can be adjusted for maintenance, oil fill, or operational use, the disclosed systems and methods for a high voltage connector simplify the installation process and reduce downtime when replacing and/or installing cables. As another advantage, the ability of the high voltage connector to bend and hold in selected positions may reduce packing space to enclose the X-ray tube assembly, thereby decreasing the overall footprint of the medical imaging device. By more reliably filling the oil envelope, incidence of high voltage instability may be reduced, and useable life of the X-ray assembly may thus be relatively increased and part replacement and service time may be decreased.

The disclosure also provides support for a high voltage connector for a medical imaging assembly, comprising: a generator side interface configured to couple to a high voltage generator, a tube side interface configured to couple to an X-ray tube, and an insulated conductor flexibly coupling the generator side interface and the tube side interface, wherein the generator side interface is positionable in an installation position and an operational position. In a first example of the system, the system further comprises: a bracket assembly, the bracket assembly configured to movably couple the generator side interface to the X-ray tube. In a second example of the system, optionally including the first example, the bracket assembly comprises a first bracket configured to couple to the generator side interface, the first bracket comprising a slot, a second bracket configured to couple to the X-ray tube and to the first bracket, and a fastener directly coupled to the second bracket and selectively directly coupled to the slot. In a third example of the system, optionally including one or both of the first and second examples, the slot comprises an open arc shape. In a fourth example of the system, optionally including one or more or each of the first through third examples, the operational position comprises the fastener directly coupled to the slot and wherein the installation position comprises the fastener free from direct contact with the slot. In a fifth example of the system, optionally including one or more or each of the first through fourth examples, the generator side interface comprises a high voltage port configured to receive a mating electrical interface of a high voltage generator cable. In a sixth example of the system, optionally including one or more or each of the first through fifth examples, the installation position comprises the high voltage port oriented upward, and a central axis of the high voltage port oriented in a positive vertical position within a first threshold range. In a seventh example of the system, optionally including one or more or each of the first through sixth examples, the mating electrical interface is a five pin version of a Federal standard termination of the high voltage generator cable. In an eighth example of the system, optionally including one or more or each of the first through seventh examples, the insulated conductor comprises a flexible cable. In a ninth example of the system, optionally including one or more or each of the first through eighth examples, the tube side interface comprises a substantially cylindrical member and a flange, the substantially cylindrical member comprising a plurality of electrical sockets configured to receive a plurality of electrical pins coupled to a cathode of the X-ray tube, and the flange comprising a substantially circular member with a flat side formed by a segment offset from a central axis of the flange.

The disclosure also provides support for a medical imaging assembly, comprising: an X-ray tube, and a high voltage connector coupled the X-ray tube, the high voltage connector comprising a generator side interface configured to couple to a high voltage generator, a tube side interface coupled to the X-ray tube, and an insulated conductor flexibly coupling the generator side interface and the tube side interface, wherein the generator side interface is positionable in an installation position and an operational position. In a first example of the system, the X-ray tube comprises a monopolar X-ray tube. In a second example of the system, optionally including the first example, the system further comprises: a bracket assembly, the bracket assembly movably coupling the generator side interface to the X-ray tube. In a third example of the system, optionally including one or both of the first and second examples, the bracket assembly comprises a first bracket configured to couple to the generator side interface, the first bracket comprising a slot, a second bracket configured to couple to the X-ray tube and to the first bracket, and a fastener directly coupled to the second bracket and selectively directly coupled to the slot, wherein the slot comprises an open arc shape. In a fourth example of the system, optionally including one or more or each of the first through third examples, the operational position comprises the fastener directly coupled to the slot, and wherein the installation position comprises the fastener free from direct contact with the slot.

The disclosure also provides support for an imaging system, comprising: a high voltage generator, a high voltage generator cable coupled to the high voltage generator, a medical imaging device comprising an X-ray tube, and a high voltage connector comprising a generator side interface coupled the high voltage generator cable, a tube side interface coupled to the X-ray tube, and an insulated conductor flexibly coupling the generator side interface and the tube side interface, wherein the generator side interface is positionable in an installation position and an operational position. In a first example of the system, the medical imaging device is a C-arm interventional radiology system. In a second example of the system, optionally including the first example, the high voltage generator cable comprises five conductors and a five pin version of a Federal standard termination. In a third example of the system, optionally including one or both of the first and second examples, the high voltage generator cable is configured to couple to the high voltage generator in a first location and couple to the medical imaging device in a second location, wherein the first location and the second location are spaced apart by one or more of a wall, a ceiling, and a floor. In a fourth example of the system, optionally including one or more or each of the first through third examples, the generator side interface comprises a high voltage port configured to receive a mating electrical interface of the high voltage generator cable, and wherein the installation position comprises the high voltage port oriented upward, and a central axis of the high voltage port oriented in a positive vertical position within a first threshold range.

As used herein, an element or step recited in the singular and proceeded with the word “a” or “an” should be understood as not excluding plural of said elements or steps, unless such exclusion is explicitly stated. Furthermore, references to “one embodiment” of the present invention are not intended to be interpreted as excluding the existence of additional embodiments that also incorporate the recited features. Moreover, unless explicitly stated to the contrary, embodiments “comprising,” “including,” or “having” an element or a plurality of elements having a particular property may include additional such elements not having that property. The terms “including” and “in which” are used as the plain-language equivalents of the respective terms “comprising” and “wherein.” Moreover, the terms “first,”

"second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A high voltage connector for a medical imaging assembly, comprising:

a generator side interface configured to couple to a high voltage generator, a tube side interface configured to couple to an X-ray tube, and an insulated conductor flexibly coupling the generator side interface and the tube side interface, wherein the generator side interface is positionable in an installation position and an operational position.

2. The high voltage connector of claim 1, further comprising a bracket assembly, the bracket assembly configured to movably couple the generator side interface to the X-ray tube.

3. The high voltage connector of claim 2, wherein the bracket assembly comprises a first bracket configured to couple to the generator side interface, the first bracket comprising a slot, a second bracket configured to couple to the X-ray tube and to the first bracket, and a fastener directly coupled to the second bracket and selectively directly coupled to the slot.

4. The high voltage connector of claim 3, wherein the slot comprises an open arc shape.

5. The high voltage connector of claim 3, wherein the operational position comprises the fastener directly coupled to the slot and wherein the installation position comprises the fastener free from direct contact with the slot.

6. The high voltage connector of claim 1, wherein the generator side interface comprises a high voltage port configured to receive a mating electrical interface of a high voltage generator cable.

7. The high voltage connector of claim 6, wherein the installation position comprises the high voltage port oriented upward, and a central axis of the high voltage port oriented in a positive vertical position within a first threshold range.

8. The high voltage connector of claim 6, wherein the mating electrical interface is a five pin version of a Federal standard termination of the high voltage generator cable.

9. The high voltage connector of claim 1, wherein the insulated conductor comprises a flexible cable.

10. The high voltage connector of claim 1, wherein the tube side interface comprises a substantially cylindrical member and a flange, the substantially cylindrical member comprising a plurality of electrical sockets configured to receive a plurality of electrical pins coupled to a cathode of the X-ray tube, and the flange comprising a substantially circular member with a flat side formed by a segment offset from a central axis of the flange.

11. A medical imaging assembly, comprising:

an X-ray tube; and a high voltage connector coupled the X-ray tube, the high voltage connector comprising a generator side interface configured to couple to a high voltage generator, a tube side interface coupled to the X-ray tube, and an insulated conductor flexibly coupling the generator side interface and the tube side interface, wherein the generator side interface is positionable in an installation position and an operational position.

12. The medical imaging assembly of claim 11, wherein the X-ray tube comprises a monopolar X-ray tube.

13. The medical imaging assembly of claim 11, further comprising a bracket assembly, the bracket assembly movably coupling the generator side interface to the X-ray tube.

14. The medical imaging assembly of claim 13, wherein the bracket assembly comprises a first bracket configured to couple to the generator side interface, the first bracket comprising a slot, a second bracket configured to couple to the X-ray tube and to the first bracket, and a fastener directly coupled to the second bracket and selectively directly coupled to the slot, wherein the slot comprises an open arc shape.

15. The medical imaging assembly of claim 14, wherein the operational position comprises the fastener directly coupled to the slot, and wherein the installation position comprises the fastener free from direct contact with the slot.

16. An imaging system, comprising:

a high voltage generator;

a high voltage generator cable coupled to the high voltage generator;

a medical imaging device comprising an X-ray tube; and a high voltage connector comprising a generator side interface coupled the high voltage generator cable, a tube side interface coupled to the X-ray tube, and an insulated conductor flexibly coupling the generator side interface and the tube side interface, wherein the generator side interface is positionable in an installation position and an operational position.

17. The imaging system of claim 16, wherein the medical imaging device is a C-arm interventional radiology system.

18. The imaging system of claim 16, wherein the high voltage generator cable comprises five conductors and a five pin version of a Federal standard termination.

19. The imaging system of claim 16, wherein the high voltage generator cable is configured to couple to the high voltage generator in a first location and couple to the medical imaging device in a second location, wherein the first location and the second location are spaced apart by one or more of a wall, a ceiling, and a floor.

20. The imaging system of claim 16, wherein the generator side interface comprises a high voltage port configured to receive a mating electrical interface of the high voltage generator cable, and wherein the installation position comprises the high voltage port oriented upward, and a central axis of the high voltage port oriented in a positive vertical position within a first threshold range.

* * * * *